United States Patent [19]

Collins et al.

[11] 3,997,535
[45] Dec. 14, 1976

[54] QUINOXALINE-2-CARBOXAMIDOTETRAZOLES

[75] Inventors: Ian Collins, London, England; Gwynn Pennant Ellis, Rhiwbina, Wales

[73] Assignee: Allen & Hanburys Limited, London, England

[22] Filed: Mar. 11, 1974

[21] Appl. No.: 449,992

[30] Foreign Application Priority Data

Mar. 16, 1973 United Kingdom ............ 12742/73
Mar. 16, 1973 United Kingdom ............ 12743/73

[52] U.S. Cl. .................. 260/250 Q; 260/247.2 A; 424/248; 424/250
[51] Int. Cl.² ...................................... C07D 241/00
[58] Field of Search ................ 260/250 Q, 250 QN

[56] References Cited

UNITED STATES PATENTS 3,660,398 5/1972 Ley et al. .................. 260/250 QN
3,660,401 5/1972 Berkelhammer et al. ... 260/250 QN

FOREIGN PATENTS OR APPLICATIONS 1,188,249 4/1970 United Kingdom ........ 260/250 QN
1,308,370 2/1973 United Kingdom ........ 260/250 QN

*Primary Examiner*—Paul J. Killos
*Attorney, Agent, or Firm*—Bacon & Thomas

[57] ABSTRACT

Compounds of the general formula I:

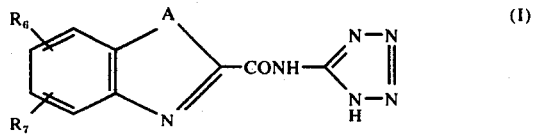

and pharmaceutically acceptable salts thereof in which:

A represents the group

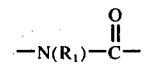

or the group

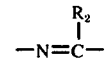

linked to the adjacent benzene ring through the nitrogen atom, in which $R_1$ represents a hydrogen atom, or an alkyl group which may optionally be substituted by one or more aryl, aryloxy, alkoxy, acyloxy, amino, alkylamino, dialkylamino or hydroxy groups or represents an alkenyl group;

$R_2$ represents a hydrogen atom, a halogen atom or an alkyl group or the group $OR_3$, where $R_3$ is a hydrogen atom or an alkyl group which may optionally be substituted by one or more aryl, aryloxy, alkoxy, acyloxy, hydroxy, amino, alkylamino or dialkylamino groups or the group $NR_4R_5$ where $R_4$ and $R_5$ may be the same or different and have the meanings given for $R_1$ or $R_4$ and $R_5$ together with the nitrogen atom form a 5 or 6 membered heterocyclic ring which may optionally contain additional hetero atoms;

$R_6$ and $R_7$ which may be the same or different represent a hydrogen atom, or a halogen atom or an alkyl group or the group $OR_3$ or the group $NR_4R_5$ as defined above. These compounds have activity as for the treatment of conditions caused primarily by the combination of an antigen with a reaginic antibody.

17 Claims, No Drawings

QUINOXALINE-2-CARBOXAMIDOTETRAZOLES

This invention relates to novel quinoxaline-2-carboxamidotetrazole derivatives which have been found to have a useful profile of pharmacological activity. It also relates to a process for production thereof, to pharmaceutical compositions containing them and to the use thereof in therapy.

The invention provides compounds of the general formula I below and pharmaceutically acceptable salts thereof:

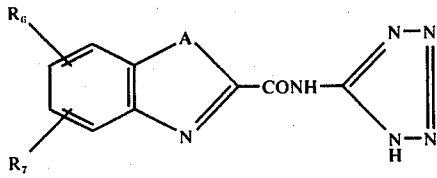

in which:

A represents the group

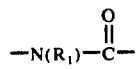

or the group

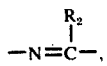

linked to the adjacent benzene ring through the nitrogen atom, and in which $R_1$ represents a hydrogen atom, or an alkyl group which may optionally be substituted by one or more aryl, aryloxy, alkoxy, acyloxy, amino, alkylamino, dialkylamino or hydroxy groups or represents an alkenyl group;

$R_2$ represents a hydrogen atom, a halogen atom or an alkyl group or the group $OR_3$, where $R_3$ is a hydrogen atom or an alkyl group which may optionally be substituted by one or more aryl, aryloxy, alkoxy, acyloxy, hydroxy, amino, alkylamino or dialkylamino groups or the group $NR_4R_5$ where $R_4$ and $R_5$ may be the same or different and have the meanings given for $R_1$ or $R_4$ and $R_5$ together with the nitrogen atom form a 5 or 6 membered heterocyclic ring which may optionally contain additional hetero atoms;

$R_6$ and $R_7$ which may be the same or different represent a hydrogen atom, or a halogen atom or an alkyl group or the group $OR_3$ or the group $NR_4R_5$ as defined above.

It will be appreciated that where $R_1$ is hydrogen the compound can exist in the tautomeric form in which $R_3$ is hydrogen. Such tautomeric forms are encompassed by the invention.

The term "alkyl" when used above to define a single group or part of a group refers to a straight or branched chain alkyl group containing 1 to 6 carbon atoms, and preferably 1 to 4 carbon atoms, and the term "alkenyl" refers to a straight or branched chain alkenyl group containing 2 to 6 carbon atoms and preferably 3 to 5 carbon atoms. The terms "aryl" and "aryloxy" preferably refer to phenyl and phenoxy groups respectively.

The term "acyloxy" preferably refers to an alkanoyloxy group containing 1 to 6 carbon atoms e.g. formyloxy, acetyloxy propionyloxy. The term "5 or 6 membered heterocyclic ring" preferably refers to a pyrrolidinyl, piperidino, morpholino, piperazinyl or N-substituted piperazinyl group.

Preferred classes of compounds are those in which the following groups have the meanings given.

$R_1$: hydrogen, alkyl, particularly methyl or ethyl, alkenyl, particularly allyl, hydroxyalkyl, particularly 2-hydroxyethyl, alkoxyalkyl, particularly 2-methoxyethyl, acyloxyalkyl, particularly 2-formyloxyethyl, dialkylaminoalkyl, particularly 3-dimethylaminopropyl.

$R_2$: hydrogen, halogen particularly chlorine, alkoxy, particularly methoxy, hydroxyalkoxy, particularly 2-hydroxyethoxy, alkoxyalkoxy, particularly 2-methoxy ethoxy, aryloxyalkoxy, particularly 2-phenoxyethoxy, dialkylaminoalkoxy, particularly 2-(dimethylaminoethoxy), alkylamino, particularly methylamino or butylamino, dialkylamino, particularly dimethylamino, hydroxyalkylamino, particularly 2-hydroxyethylamino, dialkylaminoalkylamino, particularly 2-dimethylaminoethylamino, or a morpholino group.

$R_6$ and $R_7$: hydrogen, halogen, particularly chlorine or fluorin, alkyl, particularly methyl, alkoxy, particularly methoxy, or a morpholino group.

Specific preferred compounds are those of the classes given above or salts thereof the preparation of which is described in the Examples.

The invention includes pharmaceutically acceptable salts of compounds of formula I. Salts may be formed with inorganic bases and particularly useful salts include those of the alkali metals e.g. sodium, or with organic amines e.g. dimethylamine, dimethylaminoethanol or 2-aminoethanol. When basis groups are present the invention also covers addition salts with organic or inorganic acids.

The compounds of the invention show promise as agents for the treatment of conditions in which combination of an antigen with a reaginic antibody is primarily responsible, for example extrinsic asthma, hay fever, urticaria, eczema or atopic dermatitis. Thus N(1H tetrazol-5-yl)-2-quinoxalinecarboxamide (Example 1) was compared with disodium cromoglycate, which is known to be effective in the prophylactic treatment of asthma. It was shown to be about 10 times as active as disodium cromoglycate in inhibiting release of histamine in the passive peritoneal anaphylaxis induced in rats with the DNP - egg albumen system (J. Exp. Med. 1969, 127, 727).

The invention also provides pharmaceutical compositions which contain a compound of general formula (I) or a salt thereof together with a pharmaceutically acceptable carrier, excipient, or other formulatory agent. The compositions may also contain supplementary medicinal agents, e.g. bronchodilators. Suitable forms of oral administration include tablets, capsules, syrups, or emulsions. For administration by inhalation the compositions according to the invention may be in the form of a powder or snuff or as an aerosol spray presentation. The latter may conveniently be a pressurized pack with a metering valve to deliver a fixed dosage unit or may be an aqueous solution delivered via a nebuliser.

The dosage at which the active ingredient is administered may vary within a wide range, depending on the age, weight and condition of the patient. A suitable oral dosage range is generally from 20-1500 mg and for inhalation is from 1.0-20 mg. The dose may be repeated if required.

The invention also provides a process for the preparation of compounds of formula I in which a 2-quinoxaline carboxylic acid of formula II or an activated derivative thereof, where in A, $R_6$ and $R_7$ have the meanings stated above or are convertible there into, is condensed with 5-aminotetrazole (III):

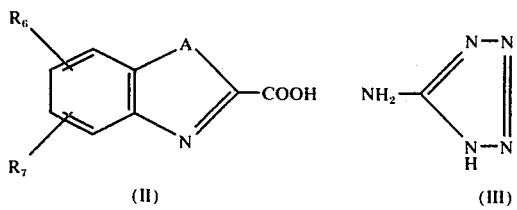

The condensation of the quinoxaline carboxylic acid (II) with 5-aminotetrazole (III) may be effected with the aid of a variety of condensing agents which are of general application for the formation of amide bonds. One such reagent, N,N'-carbonyldiimidazole, is particularly useful and condensations using this reagent are preferably carried out in an aprotic solvent such as tetrahydrofuran and/or dimethylformamide. The reaction may be carried out at ambient or elevated temperatures e.g. 20°–120° C.

Suitable activated derivatives of the quonoxaline carboxylic acids (II) include the acid halide, preferably the acid chloride, or a mixed anhydride preferably the mixed anhydride derived from an acid (II) and a carbonic acid derivative e.g. ethylcarbonic acid $C_2H_5OCOOH$, or an acyl azide.

The condensation of a 2-quinoxaline carbonyl chloride derived from a quinoxaline carboxylic acid (II) with 5-aminotetrazole is preferably carried out in an aprotic solvent such as dioxan or tetrahydrofuran, or in an aqueous medium and is also preferably carried out in the presence of an acid acceptor, for example a tertiary organic base, such as pyridine, or triethylamine, or an inorganic base such as an alkali metal hydroxide, carbonate or bicarbonate e.g. sodium or potassium hydroxide, sodium or potassium carbonate or bicarbonate.

When a mixed anhydride is used as activated derivative the reaction may also be carried out in a polar aprotic solvent such as dimethylformamide, at a reaction temperature which is preferably below 10° C.

If an acyl azide is used as activated derivative the reaction is preferably carried out in a polar aprotic solvent, for example, pyridine, the reaction temperature is preferably kept below 10° C.

Compounds of the invention may also be converted into other compounds of the invention. For example, compounds (I) in which $R_1$ = an acyloxyalkyl group e.g. formyloxyalkyl may be converted into compounds in which $R_1$ = hydroxyalkyl by hydrolysis, preferably with aqueous alkali, particularly sodium or potassium hydroxide. Compounds of formula I in which $R_2$ is chlorine may be converted into compounds of formula I in which $R_2$ is a group $OR_3$ in which $R_3$ has the meanings given by treatment with an alkali metal alkoxide, $R_3OM$ preferably a sodium alkoxide and this reaction is preferably carried out in an excess of the alcohol $R_3OH$ as solvent. Also compounds of formula I in which $R_2$ is halogen preferably chlorine or $R_6$ is fluorine may be converted into compounds of formula I in which $R_2$ or $R_6$ is the group $NR_4R_5$ by treatment with the amine $NHR_4R_5$. If desired these reactions may be carried out in the presence of a solvent, for example water or an alcohol e.g. ethanol. The displacement reactions involving the group $R_2$ = halogen are preferably carried out at ambient temperature but for those reactions where $R_6$ is fluorine the reactions are preferably carried out at an elevated temperature.

The starting quinoxaline-2-carboxylic acids (II) are either known compounds or may be prepared standard literature routes (A. Weissberger, Condensed Pyridazine and Pyrazine Rings, Interscience Publishers Ltd., 1953 250). One such route for the preparation of compounds of formula (II) in which A represents the group

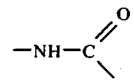

is outlined below.

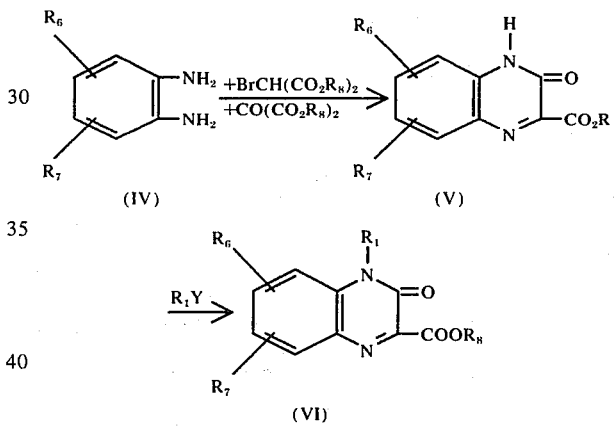

where $R_8$ = H or alkyl

The condensation of the o-phenylene diamine (IV) with an ester of 2-bromomalonic acid ($BrCH(CO_2R_8)_2$) or an ester of mesoxalic acid ($CO(CO_2R_8)_2$) gives the quinoxalin-3-one ester (V); where $R_6$ is not the same as $R_7$ a mixture of isomeric esters (V) may arise that may be separated either by fractional crystallisation or chromatography. The 2-quinoxalin-3-one ester (V) may be hydrolysed to the corresponding acid (V; $R_8$ = H) with a strong base for example sodium hydroxide.

2-Quinoxalin-3-one carboxylic acids (VI; $R_8$ = H) where $R_1$ has the meanings given other than hydrogen may be conveniently prepared from the ester (V; $R_8$ = alkyl) be alkylation followed by alkaline hydrolysis of the resulting ester (VI; $R_8$ = alkyl). Standard alkylating agents ($R_1Y$), for example alkyl halides, dialkyl-sulphates or alkylsulphonates may be used, and the reaction may advantageously be carried out in a solvent, for example acetone, 2-butanone, or dimethylformamide, and in the presence of a base for example an alkali metal carbonate such as potassium carbonate. Quinoxaline-2-carboxylic acids (II) in which A is the group ($—N=C—R_2$) and $R_2$ has the meanings given other than alkyl may be prepared via the quinoxaline-3-one (V):

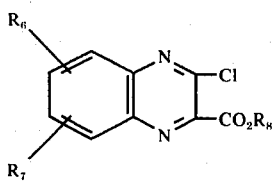

The treatment of the quinoxaline-3-one (V; $R_8$ = alkyl) with a phosphorus oxyhalide e.g. $POCl_3$ yields the 3-halo derivative (VII; $R_8$ = alkyl) which may be hydrolysed to the corresponding 2-quinoxaline carboxylic acid (VII; $R_8$ = H) by treatment with a suitable base such as sodium carbonate in an aqueous or aqueous alcoholic medium.

2-Quinoxaline carboxylic acids of the general formula (II) in which $R_2 = OR_3$ or $NR_4R_5$ may be prepared by treating the 3-halo derivative (VII; $R_8$ = alkyl) with an alkoxide e.g. sodium alkoxide $NaOR_3$ or the amine $HNR_4R_5$ followed by alkaline hydrolysis of the resulting ester. Alternatively these acids may be prepared by treating the 3-halo acid (VII; $R_8$ = H) with the appropriate amine $HNR_4R_5$ or alkoxide $OR_3$.

2-Quinoxaline carboxylic acids (II; $R_2$ = H) may be obtained from the 3-halo derivative (VII; $R_8$ = alkyl) by hydrogenolysis, for example by reaction with hydrogen in the presence of a catalyst such as palladium on barium carbonate, followed by alkaline hydrolysis of the ester group. Alternatively the 2-quinoxaline carboxylic acid (II; $R_2$ = H) may be prepared directly from the 3-halo derivative (VII; $R_8$ = H) by hydrogenolysis.

Acids of the general formula (II; A—N=CR$_2$—) in which $R_2$ = alkyl may be conveniently prepared by the reaction of the o-phenylene diamine (IV) with an $\alpha,\beta$-diketoester (VIII; $R_8$ = alkyl) followed by alkaline hydrolysis of the ester (IX). Where $R_6$ is not the same as $R_7$ a mixture of isomeric esters may arise that may be separated either by fractional crystallisation of by column chromatography.

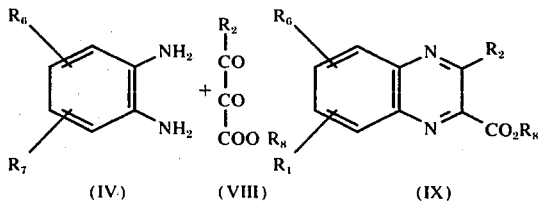

In any of the above preparations the groups $R_1 - R_7$ may be modified or introduced at any convenient point in the process. For example, acids of formula (II; A = $NR_1CO$—) in which $R_1$ is acyloxyalkyl e.g. formyloxyethyl may be prepared by acylation of the corresponding acid (II) in which R is hydroxyalkyl. 2-Quinoxaline carbonyl halides may be prepared from the corresponding 2-quinoxaline carboxylic acid (II) in a conventional manner, e.g. reaction with thionyl chloride or $PCl_5$.

The following Examples illustrate the invention:

EXAMPLE 1

N(1H-Tetrazol-5-yl)-2-quinoxalinecarboxamide

Method I

2-Quinoxalinecarbonyl chloride (19.1 g) in 1,2-dichloroethane (150 ml) was slowly added to a stirred, cooled solution of sodium bicarbonate (16.8 g) and 5-amino-1H-tetrazole (8.5 g) in water (200 ml). The mixture was stirred for 18 hours at room temperature and the solid was collected, dried and crystallised from dimethylformamide. It has m.p. 286°–287.5° (d), (49%).

Method II

2-Quinoxalinecarbonyl chloride (19 g) in dioxan (100 ml) was added during 20 minutes to a stirred mixture of 5-amino-1H-tetrazole (9.4 g) and triethylamine (15.2 g), in dioxan (100 ml). The mixture was stirred overnight and poured into water. The solution was acidified to pH2 with dilute hydrochloric acid and the solid was collected and dried. It had m.p. 284° (d) (66%).

Method III

N,N'-Carbonyldiimidazole (13.95 g) and 2-quinoxalinecarboxylic acid (15 g) in tetrahydrofuran (600 ml) were heated under reflux for 2 hours. 5-Amino-1H-tetrazole (7.32 g) in tetrahydrofuran (36 ml) and dimethylformamide (24 ml) was added and the mixture was heated under reflux for 50 minutes. The solvent was distilled off under reduced pressure and the residue was dissolved in water (300 ml). The solution was acidified to pH2 with dilute hydrochloric acid and the solid was collected and crystallised from dimethylformamide. It had m.p. 284°–285° (d) (70%).

EXAMPLE 2

N(1H-Tetrazol-5-yl)-2-quinoxalinecarboxamide, sodium salt, monohydrate

N(1H-Tetrazol-5-yl)-2-quinoxalinecarboxamide (Example 1) (10.5 g) was added to a warm solution of sodium bicarbonate (3.4 g) in water (250 ml). The solution was concentrated to 50 ml and acetone (200 ml) was added. The pale yellow crystals were collected and dried, and had m.p. 337°–338.5° (65%).

EXAMPLE 3

3,4-Dihydro-3-oxo-N(1H-tetrazol-5-yl)-2-quinoxalinecarboxamide 3,4-Dihydro-3-oxo-2-quinoxalinecarboxylic acid (1.9 g) and N,N'-carbonyldiimidazole (1.62 g) in dimethylformamide (75 ml) were stirred at room temperature for 18 hours. 5-Amino-1H-tetrazole (1.0 g) was added and stirring was continued for 3 days. The solvent was distilled off under reduced pressure and the residue was dissolved in aqueous sodium hydroxide (20 ml., 5N). The solution was filtered and acidified to pH2 with hydrochloric acid to give a yellow solid. This was crystallised from aqueous dimethylformamide and had m.p. 312°–313° (d) (43%).

In a similar manner 3,4-Dihydro-6,7-dimethyl-3-oxo-N(1H-tetrazol-5-yl)-2-quinoxalinecarboxamide, m.p. 262° (d), was prepared from 3,4-dihydro-6,7-dimethyl-3-oxo-2-quinoxalinecarboxylic acid (40%).

EXAMPLE 4

3,4-Dihydro-3-oxo-N(1-H-tetrazol-5-yl)-2-quinoxalinecarboxamide, disodium salt, dihydrate 2N Sodium hydroxide was added dropwise to 3,4-dihydro-3-oxo-N(1H-tetrazol-5-yl)-2-quinoxalinecarboxamide (100 mg) in water (25 ml) until the mixture reached pH9. The solution was evaporated and the residue was crystallised from aqueous actone and dried. The product did not melt below 400° (70%).

EXAMPLE 5

3-Chloro-N(1H-tetrazol-5-yl)-2-quinoxalinecarboxamide

3-Chloro-2-quinoxalinecarboxylic acid (1.5 g) and N,N'-carbonyldiimidazole (1.2 g) in tetrahydrofuran (50 ml) were heated under reflux for 15 minutes. 5-Amino-1H-tetrazole (0.7 g) in dimethylformamide (5 ml) was added and the solution heated under reflux for 1 hour. The solvent was distilled off and the residue was triturated with dilute hydrochloric acid (25 ml., 2N). The solid was collected and crystallised from aqueous dimethylformamide. It had m.p. 257°–260° (d) (38%).

EXAMPLE 6

3(2-Hydroxyethylamino)-N(1H-tetrazol-5-yl)-2-quinoxalinecarboxamide, compound with 2-aminoethanol 2-Aminoethanol (20 ml) and water (10 ml) were added to 3-chloro-N(1H-tetrazol-5-yl)-2-quinoxalinecarboxamide (Example 5) (2 g) and the mixture stirred at room temperature for 1 hour. The yellow solid was collected and crystallised from ethanol. It had m.p. 219°–220° (45%).

EXAMPLE 7

3-Methylamino-N(1H-tetrazol-5-yl)-2-quinoxalinecarboxamide

Methylamine in ethanol (20 ml., 33%) and 3-chloro-N(1H-tetrazol-5-yl)-2-quinoxalinecarboxamide (Example 5) (2 g) were stirred together at room temperature for 8 hours. The yellow solid was collected and crystallised from ethanol and heated at 120° in a vacuum. It had m.p. 292° (d) (50%).

EXAMPLE 8

3-Dimethylamino-N(1H-tetrazol-5-yl)-2-quinoxalinecarboxamide, compound with dimethylamine Dimethylamine in ethanol (10 ml., 33%) and 3-chloro-N(1H-tetrazol-5-yl)-2-quinoxalinecarboxamide (Example 5) (2 g) were stirred together at room temperature for 5 hours. The yellow solid was collected and crystallised from methanol. It had m.p. 260°–265° (d).

EXAMPLE 9

3-(2-Dimethylaminoethylamino)-N(1H-tetrazol-5-yl)-2-quinoxalinecarboxamide, dihydrochloride 3-Chloro-N(1H-tetrazol-5-yl)-2-quinoxalinecarboxamide (Example 5) (2 g) and N,N-dimethylethylenediamine (10 ml) were stirred together at room temperature for 18 hours. The excess of N,N-dimethylethylenediamine was distilled off under reduced pressure. The residue was treated with dilute hydrochloric acid (25 ml., 2N) and the solid was collected and crystallised from methanol. It had m.p. 242°–243° (24%).

The following compounds were prepared in a similar manner from 3-chloro-N(1H-tetrazol-5-yl)-2-quinoxalinecarboxamide:

3-Butylamino-N(1H-tetrazol-5-yl)-2-quinoxalinecarboxamide, m.p. 236°–237° (84%) with butylamine.

3-Morpholino-N(1H-tetrazol-5-yl)-2-quinoxalinecarboxamide, m.p. 284° (d) (83%) with morpholine.

EXAMPLE 10

3(2-Hydroxyethoxy)N(1H-tetrazol-5-yl)-2-quinoxalinecarboxamide

3-Chloro-N(1H-tetrazol-5-yl)-2-quinoxalinecarboxamide (Example 5) (2 g) was added to a solution of sodium (0.33 g) in ethylene glycol (10 ml) and the mixture was stirred at room temperature for 18 hours and poured into dilute hydrochloric acid (25 ml., 2N). The solid was collected, dried and crystallised from methanol. It had m.p. 245° (40%).

The following compounds were prepared from 3-chloro-N(1H-tetrazol-5-yl)-2-quinoxalinecarboxamide and the alcohol indicated:

3-(2-Phenoxyethoxy)-N(1H-tetrazol-5-yl)-2-quinoxalinecarboxamide, m.p. 264.5°, from 2-phenoxyethanol (64%).

3-(2-Methoxyethoxy)-N(1H-tetrazol-5-yl)-2-quinoxalinecarboxamide, m.p. 246°–247°, from 2-methoxyethanol (85%).

EXAMPLE 11

3-Methoxy-N(1H-tetrazol-5-yl)-2-quinoxalinecarboxamide

3Methoxy-2-quinoxalinecarboxylic acid (1.5 g) and N,N-carbonyldiimidazole (1.2 g) in tetrahydrofuran (50 ml) were heated under reflux for 15 minutes. 5-Amino-1H-tetrazole (0.7 g) in dimethylformamide (5 ml) was added and the solution was heated under reflux for 1 hour. The crystalline solid was collected and stirred with dilute hydrochloric acid (25 ml., 2N) and the solid was filtered off and dried. It had m.p. 260° (d) (45%).

EXAMPLE 12

3,6-Dimethoxy-N(1H-tetrazol-5-yl)-2-quinoxalinecarboxamide a.
3,4-Dihydro-6-methoxy-3-oxo-2-quinoxalinecarboxylic acid, ethyl ester A solution of 4-methoxy-o-phenylenediamine (9.5 g) and triethylamine (7 g) in ethanol (100 ml) was cooled to 0°–5° and stirred in an atmosphere of nitrogen. Diethyl bromomalonate (23.7 g) in ethanol (50 ml) was added during 30 minutes. The temperature of the mixture was maintained at 0°–5° for a further 6 hours and then allowed to rise to 20° and stirred at this temperature for 16 hours. The solid was filtered off, stirred with dilute hydrochloric acid (400 ml., 0.2N), filtered off, washed with water, dried and crystallised from a mixture of ethyl acetate and methanol. It had m.p. 229° (26%).

In a similar manner, 6-chloro-3,4-dihydro-3-oxo-2-quinoxalinecarboxylic acid, ethyl ester was prepared from 4-chloro-o-phenylenediamine, m.p. 236°–238° (11%).

b. 3-Chloro-6-methoxy-2-quinoxalinecarboxylic acid, ethyl ester 3,4-Dihydro-6-methoxy-3-oxo-2-quinoxalinecarboxylic acid, ethyl ester (Example 12a) (4.8 g) and phosphoryl chloride (30 ml) were heated at 90° for 30 minutes. The solution was cooled and slowly added to iced water (300 ml). The solid was filtered off, dried and crystallised from light petroleum (b.p. 60°–80°). It had m.p. 79.5°.

In a similar manner, 3,6-dichloro-2-quinoxalinecarboxylic acid, ethyl ester, m.p. 63°–65°, was prepared from 6-chloro-3,4-dihydro-3-oxo-2-quinoxalinecarboxylic acid, ethyl ester (Example 12a) (73%).

c. 3,6-Dimethoxy-2-quinoxalinecarboxylic acid

Sodium (0.95 g) was dissolved in dry methanol (250 ml) and 3-chloro-6-methoxy-2-quinoxalinecarboxylic acid, ethyl ester (Example 12b) (4.4 g) was added. The mixture was heated under reflux for 1 hour, diluted with water (50 ml) and heated for a further 45 minutes and cooled. Hydrochloric acid (2N) was added to give a solution of pH1 and the crystalline solid that separated was collected, washed with water and dried. It had m.p. 151°–152° (85%).

In a similar manner, 6-chloro-3-methoxy-2-quinoxalinecarboxylic acid, m.p. 165°–167°, was prepared from 3,6-dichloro-2-quinoxalinecarboxylic acid, ethyl ester (Example 12b) (68%).

d. 3,6-Dimethoxy-N(1H-tetrazol-5-yl)-2quinoxalinecarboxamide 3,6-Dimethoxy-2-quinoxalinecarboxylic acid (Example 12c) (2 g) and N,N'-carbonyldiimidazole (1.4 g) in tetrahydrofuran (50 ml) were heated under reflux for 15 minutes. 5-Amino-1H-tetrazole (0.8 g) in dimethylformamide (5 ml) was added and the mixture was heated under reflux for a further 30 minutes. The solid that crystallised from the solution on cooling was collected and dried. It had m.p. 250°–251° (d) (59%).

The following compounds were prepared in a similar manner from the corresponding carboxylic acids prepared respectively as described in 12c.

6,7-Dimethoxy-N(1H-tetrazol-5-yl)-2-quinoxalinecarboxamide, m.p. 300°–302° (d) (39%).

6-Chloro-3-methoxy-N(1H-tetrazol-5-yl)-2-quinoxalinecarboxamide, m.p. 263°–265° (23%).

EXAMPLE 13

3,6,7-Trimethoxy-N(1H-tetrazol-5-yl)-2-quinoxalinecarboxamide a. 3,6,7-Trimethoxy-2-quinoxalinecarboxylic acid

3-Chloro-6,7-dimethoxy-2-quinoxalinecarboxylic acid, ethyl ester (3.5 g) was added to sodium methoxide (prepared from sodium (0.7 g) in methanol (250 ml)). The solution was heated under reflux for 2 hours. Water (50 ml) was added and the solution was heated under reflux for 45 minutes and cooled. 2N Hydrochloric acid was added to give a mixture of pH1 and the methanol was distilled off. Water (500 ml) was added and the solution was extracted with ethyl acetate. The extract was dried over magnesium sulphate, filtered and evaporated and the residue was crystallised from a mixture of ethyl acetate and light petroleum (b.p. 60°–80°). The product had m.p. 163°–164° (d) (54%).

b. 3,6,7-Trimethoxy-N(1H-tetrazol-5-yl)-2-quinoxalinecarboxamide, compound with imidazole 3,6,7-Trimethoxy-2-quinoxalinecarboxylic acid (1.7 g) and N,N'-carbonyldiimidazole (1.55 g) in a mixture of tetrahydrofuran (50 ml) and dimethylformamide (10 ml) were heated under reflux for 1 hour. 5-Amino-1H-tetrazole (0.6 g) was added and the solution was heated under reflux for 15 minutes. The solid that crystallised from the solution was collected. It had m.p. 234° (d) (77%).

c. 3,6,7-Trimethoxy-N(1H-tetrazol-5-yl)-2-quinoxalinecarboxamide 3,6,7-Trimethoxy-N(1H-tetrazol-5-yl)-2-quinoxalinecarboxamide, compound with imidazole (1.9 g) was added to 2N hydrochloric acid. The mixture was stirred and the solid was collected and dried. The product had m.p. 270°–272° (100%).

EXAMPLE 14

3-Chloro-6,7-dimethyl-N(1H-tetrazol-5-yl)-2-quinoxalinecarboxamide a. 3-Chloro-6,7-dimethyl-2-quinoxalinecarboxylic acid, ethyl ester 3,4-Dihydro-6,7-dimethyl-4-oxo-2-quinoxalinecarboxylic acid, ethyl ester (24.6 g) and phosphoryl chloride (60ml) were heated at 100° for 1 hour, allowed to cool and poured onto ice (500 g). Aqueous ammonia was added to give a mixture pH3 and the solid was collected and crystallised from aqueous acetone. It had m.p. 109°–111° (95%).

b. 3-Chloro-6,7-dimethyl-2-quinoxalinecarboxylic acid

3Chloro-6,7-dimethyl-2-quinoxalinecarboxylic acid, ethyl ester (14.5 g) and sodium carbonate (3.2 g) in methanol (300 ml) and water (75 ml) were heated under reflux for 2 hours. The methanol was distilled off and the aqueous solution was acidified with dilute hydrochloric acid. The solid was collected, dried and crystallised from a mixture of ethyl acetate and light petroleum (b.p. 60°–80°). It had m.p. 146.5°–148.5° (d) (75%).

c. 3-Chloro-6,7-dimethyl-N(1H-tetrazol-5-yl)-2-quinoxalinecarboxamide

3-Chloro-6,7-dimethyl-2quinoxalinecarboxylic acid (10.5 g) and N,N'-carbonyldiimidazole (7.35 g) in tetrahydrofuran (350 ml) were heated under reflux for 1 hour. 5-Amino-1H-tetrazole (4.3 g) in dimethylformamide (10 ml) was added and the mixture was heated under reflux for a further hour and cooled. The solid was collected and dissolved in aqueous dimethylaminoethanol. Dilute hydrochloric acid was added to the solution and the solid was collected and crystallised from dimethylformamide. The product decomposed at 360° (39%).

EXAMPLE 15

3-(2-Dimethylaminoethoxy)-6,7-dimethyl-N(1H-tetrazol-5-yl)-2-quinoxalinecarboxamide, hydrochloride 3-Chloro-6,7-dimethyl-N(1H-tetrazol-5-yl)-2-quinoxalinecarboxamide (Example 14) (3 g) was added to a solution of sodium (0.46 g) in 2-dimethylaminoethanol (20 ml) and the mixture was heated at 100° in an atmosphere of nitrogen for 5.5 hours and evaporated. The residue was dissolved in water and the solution was acidified with dilute hydrochloric acid. The solid was crystallised from dimethylformamide and had m.p. 247°–248° (d) (15%).

EXAMPLE 16

6,7-Dimethyl-N(1H-tetrazol-5-yl)-2-quinoxalinecarboxamide a. 6,7-Dimethyl-2-quinoxalinecarboxylic acid

3-Chloro-6,7-dimethyl-2-quinoxalinecarboxylic acid, ethyl ester (Example 14a) (6.0 g), palladium chloride (0.4 g) and barium carbonate (17.4 g) in ethanol (500 ml) containing water (6 ml) were stirred in an atmosphere of hydrogen at room temperature and atmospheric pressure for 18 hours. The mixture was filtered and the filtrate was evaporated. The residue was crystallised from a mixture of ethyl acetate and light petroleum (b.p. 60°–80°). The solid was dissolved in aqueous sodium hydroxide (20 ml., 2N) and ethanol (20 ml) and the solution was heated under reflux for 10 minutes and cooled. Hydrochloric acid was added and the solid was collected and crystallised from aqueous ethanol. It had m.p. 214.5°–216° (20%).

b. 6,7Dimethyl-N(1H-tetrazol-5-yl)-2-quinoxalinecarboxamide 6,7-Dimethyl-2-quinoxalinecarboxylic acid (0.7 g) and N,N'-carbonyldiimidazole (0.84 g) in dimethylformamide (10 ml) were stirred and heated at 60° for 6 hours. 5Amino-1H-tetrazole (0.66 g) was added and the mixture was stirred and heated at 60° for a further 30 minutes. The solid was collected and dissolved in aqueous dimethylaminoethanol. Aqueous acetic acid was added and the solid was collected and dried. It had m.p. 304° (d) (46%).

EXAMPLE 17

3,4-Dihydro-4-methyl-3-oxo-N(1H-tetrazol-5-yl)-2-quinoxalinecarboxamide a.
3,4-Dihydro-4-methyl-3-oxo-N(1H-tetrazol-5-yl)-2-quinoxalinecarboxamide, compound with imidazole 3,4-Dihydro-4-methyl-3-oxo-2-quinoxalinecarboxylic acid (3 g) and N,N'-carbonyldiimidazole (2.4 g) in tetrahydrofuran (100 ml) and dimethylformamide (55 ml) were heated under reflux for 1 hour. 5-Amino-1H-tetrazole (1.25 g) in dimethylformamide (10 ml) was added and the solution was heated under reflux for 1.5 hours. The solution was concentrated and the solid that crystallised was collected. It had m.p. 237° (d).

b.
3,4-Dihydro-4-methyl-3-oxo-N(1H-tetrazol-5-yl)-2-quinoxalinecarboxamide 3,4-Dihydro-4-methyl-3-oxo-N(1H-tetrazol-5-yl)-2-quinoxalinecarboxamide, compound with imidazole (1.3 g) was treated with hydrochloric acid (25 ml., 2N). The solid was collected and crystallised from aqueous dimethylformamide. It had m.p. 288° (d).

EXAMPLE 18

4-Allyl-3,4-dihydro-3-oxo-N(1H-tetrazol-5-yl)-2-quinoxalinecarboxamide, compound with imidazole a. 4-Allyl-3,4-dihydro-3-oxo-2-quinoxalinecarboxylic acid, ethyl ester 3,4-Dihydro-3-oxo-2-quinoxalinecarboxylic acid, ethyl ester (5 g), allyl bromide (2.8 g) and anhydrous potassium carbonate (15 g) in butanone (100 ml) were stirred and heated under reflux for 3 hours and cooled. The solid was filtered off and the filtrate was evaporated. The residue was crystallised from cyclohexane to give a yellow solid, which had m.p. 77°–79° (56%).

In a similar manner:
3,4-Dihydro-4-(2-methoxyethyl)-3-oxo-2-quinoxalinecarboxylic acid, ethyl ester, an oil that did not crystallise, was prepared from 3,4-Dihydro-3-oxo-2-quinoxalinecarboxylic acid and 2-methoxyethyl p-toluene sulphonate and 4-(3-dimethylaminopropyl)-3,4-dihydro-6,7-dimethyl-3-oxo-2-quinoxalinecarboxylic acid, ethyl ester, an oil that did not crystallise, was prepared from 3,4-dihydro-6,7-dimethyl-3-oxo-2-quinoxalinecarboxylic acid, ethyl ester and N,N-dimethyl-3-chloropropylamine.

b. 4-Allyl-3,4-dihydro-3-oxo-2quinoxalinecarboxylic acid

4-Allyl-3,4-dihydro-3-oxo-2-quinoxalinecarboxylic acid, ethyl ester (3.3 g) in 2N sodium hydroxide (50 ml) was heated on a steam bath for 15 minutes. 2N Hydrochloric acid (50 ml) was added and the solid was collected and dried. It had m.p. 145°–148° (57%).

The following compounds were prepared in a similar way:

3,4-Dihydro-4(2-methoxyethyl)-3-oxo-2-quinoxalinecarboxylic acid, m.p. 158°–160° from the ester prepared in (a) above.

4-(3-Dimethylaminopropyl)-3,4-dihydro-6,7-dimethyl-3-oxo-2-quinoxalinecarboxylic acid, isolated as its hydrochloride, which was crystallised from dimethylformamide and had m.p. 257°–258° (d), from the ester prepared as in (a) above.

c.
4-Allyl-3,4-dihydro-3-oxo-N(1H-tetrazol-5-yl)-2-quinoxalinecarboxamide, compound with imidazole 4-Allyl-3,4-dihydro-3-oxo-2-quinoxalinecarboxylic acid (1.6 g) and N,N'-carbonyldiimidazole (1.2 g) in tetrahydrofuran (30 ml) were heated under reflux for 0.5 hours. 5-Amino-1H-tetrazole (0.5 g) in dimethylformamide (5 ml) was added and the mixture was heated under reflux for 3 hours. The solid was collected and recrystallised from water and had m.p. 225°–229° (36%).

The following compound was prepared in a similar manner:

3,4-Dihydro-4-(2-methoxyethyl)-3-oxo-N(1H-tetrazol-5-yl)-2quinoxalinecarboxamide, compound with imidazole, m.p. 206°–207.5° (85%), from the carboxylic acid prepared as in (b) above.

EXAMPLE 19

4-(3-Dimethylaminopropyl)-3,4-dihydro-6,7-dimethyl-3-oxo-N(1H-tetrazol-5-yl)-2-quinoxalinecarboxamide, hydrochloride 4-(3-Dimethylaminopropyl)-3,4-dihydro-6,7-dimethyl-3-oxo-2-quinoxalinecarboxylic acid, hydrochloride (Example 18b) (0.26 g) and N,N'-carbonyldiimidazole (0.14 g) in dimethylformamide (5 ml) were heated at 100° for 5.5 hours. 5-Amino-1H-tetrazole (0.78 g) was added and heating at 100° was continued for 1 hour. The solid was collected and dissolved in hot aqueous dimethylaminoethanol (8 ml) (5%) and the solution was acidified with 2N hydrochloric acid. The solid that crystallised as the solution cooled was collected and dried. It had m.p. 280°–283° (d) (14%).

EXAMPLE 20

4(2-Formyloxyethyl)-3,4-dihydro-3-oxo-N(1H-tetrazol-5-yl)-2-quinoxalinecarboxamide a.
3,4-Dihydro-4(2-hydroxyethyl)-3-oxo-2-quinoxalinecarboxylic acid, ethyl ester 3,4-Dihydro-3-oxo-2-quinoxalinecarboxylic acid, ethyl ester (1 g), 2-bromoethanol (1.15 g) and anhydrous potassium carbonate (3 g) were heated under reflux in butanone (100 ml) for 5 hours. The mixture was cooled and the solid was filtered off. The filtrate was evaporated to give an oil which was crystallised from a mixture of benzene and light petroleum (b.p. 60°–80°). It had m.p. 137°–138°.

b.
3,4-Dihydro-4(2-hydroxyethyl)-3-oxo-2-quinoxalinecarboxylic acid 3,4-Dihydro-4(2-hydroxyethyl)-3-oxo-2-quinoxalinecarboxyic acid, ethyl ester (10 g) in aqueous sodium hydroxide (100 ml., 2N) was warmed at 80°–100° for 5 minutes. The yellow solution was acidified with hydrochloric acid (2N) and the solid that crystallised was collected and dried. It had m.p. 195° (d).

c.
4(2-Formyloxyethyl)-3,4-dihydro-3-oxo-2-quinoxalinecarboxylic acid

Formic acid (3 ml., 98%) was added dropwise to acetic anhydride (6 ml) which was cooled below 5°. The mixture was heated at 50° for 15 minutes and cooled to below 5° and added slowly to a cold (5°–10°) solution of 3,4-dihydro-4(2-hydroxyethyl)-3-oxo-2-quinoxalinecarboxylic acid (3.2 g) in pyridine (40 ml). The solution was allowed to warm to room temperature, stirred for 6 hours and the pyridine was distilled off under reduced pressure. Hydrochloric acid (50 ml., 2N) was added to the residue and the solid was filtered off and dried, m.p. > 100°. Attempts to recrystallise this compound from dimethylformamide resulted in the loss of the formyl group.

d.
4(2-Formyloxyethyl)-3,4-dihydro-3-oxo-N(1H-tetrazol-5-yl)-2-quinoxalinecarboxamide 4(2-Formyloxyethyl)-3,4-dihydro-3-oxo-2-quinoxalinecarboxylic acid (1 g) and N,N′-carbonyldiimidazole (0.6 g) in dry tetrahydrofuran (100 ml) were heated under reflux for 15 minutes. 5-Amino-1H-tetrazole (0.5 g) in dimethylformamide (5 ml) was added and the mixture was heated under reflux for 1 hour. The solid was collected and treated with aqueous hydrochloric acid (25 ml., 2N). It was filtered off, dried and crystallised from aqueous dimethylformamide. It had m.p. 240°–241° (d).

EXAMPLE 21

3,4-Dihydro-4(2-hydroxyethyl)-3-oxo-N(1H-tetrazol-5-yl)-2-quinoxalinecarboxamide 4(2-Formyloxyethyl)-3,4-dihydro-3-oxo-N(1H-tetrazol-5-yl)-2-quinoxalinecarboxamide (Example 20d) (1.85 g) in water (100 ml) was treated with sodium hydroxide (5.9 ml., 2N) and the solution was stirred for 30 minutes at room temperature. Hydrochloric acid (6 ml., 2N) was added and the solid was collected and crystallised from aqueous dimethylformamide and dried. It had m.p. 269° (d).

EXAMPLE 22

4-Ethyl-6-fluoro-3,4-dihydro-3-oxo-N(1H-tetrazol-5yl)-2-quinoxalinecaroboxamide a.
6-Fluoro-3,4-dihydro-3-oxo-2-quinoxalinecarboxylic acid, ethyl ester and
7-fluoro-3,4-dihydro-3-oxo-2-quinoxalinecarboxylic acid, ethyl ester Triethylamine (5 ml) was added dropwise to a solution of 4-fluoro-o-phenylenediamine hydrochloride (7.2 g) and diethyl mesoxalate (7.85 g) in ethanol (100 ml) and the mixture was heated under reflux for 1 hour and evaporated. The residue was crystallised from aqueous ethanol to give a mixture of the two esters, m.p. 186°–189°, (19%).

b.
4-Ethyl-6-fluoro-3,4-dihydro-3-oxo-2-quinoxalinecarboxylic acid, ethyl ester The mixture of 6-fluoro-3,4-dihydro-3-oxo-2-quinoxalinecarboxylic acid, ethyl ester and 7-fluoro-3,4-dihydro-3-oxo-2-quinoxalinecarboxylic acid, ethyl ester (Example 22a) (2 g), ethyl iodide (4 g) and anhydrous potassium carbonate (5.9 g) in 2-butanone (200 ml) were heated under reflux for 5 hours. The mixture was filtered and the filtrate was evaporated. The residual oil was chromatographed on silica using a mixture of petroleum ether (b.p. 60°–80°) and ethyl acetate (3:1) as eluent to give the required product, on evaporation of the later fractions, m.p. 99°–101.5°, (50%).

c.
4-Ethyl-6-fluoro-3,4-dihydro-3-oxo-2-quinoxalinecarboxylic acid

4-Ethyl-6-fluoro-3,4-dihydro-3-oxo-2-quinoxalinecarboxylic acid, ethyl ester (8 g) and sodium carbonate (0.25 g) in methanol (20 ml) and water (10 ml) were heated under reflux for 2 hours. The methanol was distilled off and the aqueous solution was acidified with hydrochloric acid and the solid was collected. It had m.p. 162.5°–164° (39%).

d.
4-Ethyl-6-fluoro-3,4-dihydro-3-oxo-N(1H-tetrazol-5-yl)-2-quinoxalinecarboxamide, compound with imidazole 4-Ethyl-6-fluoro-3,4-dihydro-3-oxo-3-quinoxalinecarboxylic acid (300 mg) and N,N′-carbonyldiimidazole (220 mg) in tetrahydrofuran (15 ml) were heated under reflux for 1 hour. 5-Amino-1H-tetrazole (125 mg) in dimethylformamide (1 ml) was added and the mixture was heated a further 1.5 hours and cooled. The solid was collected and crystallised from a mixture of dimethylformamide and ether. It had m.p. 205°–206° (91%).

e.
4-Ethyl-6-fluoro-3,4-dihydro-3-oxo-N(1H-tetrazol-5-yl)-2-quinoxalinecarboxamide 4-Ethyl-6-fluoro-3,4-dihydro-3-oxo-N(1H-tetrazol-5-yl)-2-quinoxalinecarboxamide, compound with imidazole (300 mg) was dissolved in aqueous 2-dimethylaminoethanol and the solution was acidified with dilute hydrochloric acid. The solid was collected and dried and had m.p. 271°–271.5°.

EXAMPLE 23

4-Ethyl-3,4-dihydro-6-morpholino-3-oxo-N(1H-tetrazol-5-yl)-2-quinoxalinecarboxamide 4-Ethyl-6-fluoro-3,4-dihydro-3-oxo-N(1H-tetrazol-5-yl)-2-quinoxaline-2-carboxamide (100 mg) and morpholine (300 mg) in water (0.3 ml) were heated at 120° for 5 hours and cooled. The mixture was acidified with acetic acid and the solid was collected and dried. It had m.p. 308°–309.5°.

EXAMPLE 24

3,4-Dihydro-6-methoxy-4-methyl-3-oxo-N(1H-tetrazol-5-yl)-2-quinoxalinecarboxamide a.
3,4-Dihydro-6-methoxy-3-oxo-2-quinoxalinecarboxylic acid, ethyl ester

A solution of 4-methoxy-o-phenylenediamine (9.5 g) and triethylamine (7 g) in ethanol (100 ml) was cooled to 0°–5° and stirred in an atmosphere of nitrogen. Diethyl bromomalonate (23.7 g) in ethaol (50 ml) was added during 30 minutes. The temperature of the mixture was maintained at 0°–5° for a further 6 hours and then allowed to rise to 20° and stirred at this temperature for 16 hours. The solid was filtered off, stirred with dilute hydrochloric acid (400 ml., 0.2N), filtered off, washed with water, dried and crystallised from a mixture of ethyl acetate and methanol, m.p. 229°.

b.
3,4-Dihydro-6-methoxy-4-methyl-3-oxo-2-quinoxalinecarboxylic acid, ethyl ester 3,4-Dihydro-6-methoxy-3-oxo-2-quinoxalinecarboxylic acid, ethyl ester (1.9 g), methyl iodide (2 ml) and anhydrous potassium carbonate (6 g) in 2-butanone (100 ml) were stirred and heated under reflux for 1.5 hours. The solid was filtered off and the filtrate was evaporated. The residue was crystallised from aqueous methanol, m.p. 166° (80%).

c.
3,4-Dihydro-6-methoxy-4-methyl-3-oxo-2-quinoxalinecarboxylic acid 3,4-Dihydro-6-methoxy-4-methyl-3-oxo-2-quinoxalinecarboxylic acid, ethyl ester (1.5 g) and aqueous sodium hydroxide (25 ml., 2N) were heated on a steam bath for 5 minutes. The solution was acidified with dilute hydrochloric acid to pH1 and the solid was collected and dried, m.p. 223° (d) (100%).

d.
3,4-Dihydro-6-methoxy-4-methyl-3-oxo-N(1H-tetrazol-5-yl)-2-quinoxalinecarboxamide 3,4-Dihydro-6-methoxy-4-methyl-3-oxo-2-quinoxalinecarboxylic acid (1.2 g) and N,N'-carbonyldiimidazole (0.8 g) in tetrahydrofuran (25 ml) and dimethylformamide (20 ml) were heated under reflux for 1 hour. 5-Amino-1H-tetrazole (0.5 g) in dimethylformamide (5 ml) was added and the solution was heated under reflux for 1 hour and allowed to cool. The solid was collected and dried, m.p. 295°–296° (d) (70%).

EXAMPLE 25

Pharmaceutical Compositions (In this Example AH 9932 is the compound of Example 1 and AH 9932V is the sodium salt as described in Example 2)

a. Inhalation aerosol

To prepare 100 aerosol cans, each of which delivers 200 metered doses of 1.0 mg AH 9932

Micronise AH 9932V to give a powder in which nearly all the particles are smaller than 5 μm in diameter. Dissolve 0.60 g. of Emulsifier YN 100 (Emulsifier YN 100 is a grade of the ammonium salt of synthetic lecithin, supplied by Cadbury Bros.) in 570 g. of trichlorofluoromethane (Arcton 11) at 0° C. Disperse in this solution with a high shear mixer 28.8 g. of micronised AH 9932V. Meter 5.7 g. fractions of the drug suspension into suitable aluminium cans and seal the cans by crimping on suitable pressure-filling aerosol valves capable of metering 85 mg doses of final product. Inject through the valve into each can 14.7 g. of dichlorodifluoromethane (Arcton 12). Fit a suitable oral adaptor/actuator unit on to each can.

b. Tablets

To prepare 10,000, each containing 200 mg AH 9932

Mix together 2.200 kg of AH 9932V (sieved 60 mesh) with 2.00 kg lactose B.P. and 100 g of maize starch. Evenly moisten the mixed powders with sufficient water to produce a cohesive mass, pass this through a 16 mesh sieve and dry the granules at 50° C in a fluidised bed dryer. Blend the dry granules with 100 g of maize starch and 10 g magnesium stearate. Compress on a suitable tablet press to give tablets each weighing 440 mg.

c. Capsules (for oral use)

To prepare 10,000 hard gelatin capsules containing AH 9932

Mix the powdered AH 9932V (sieved 60 mesh) with sufficient Sta-Ex starch 1500 (Sta-Ex starch 1500 is a grade of free-flowing starch supplied by A. E. Staley & Co. Ltd., London) and magnesium stearate equivalent to 1% of the total powder-weight, to give the required dosage, which can be up to 250 mg AH 9932. Fill into No. 1 hard gelatin capsules with a suitable capsulating machine.

d. Capsules for inhalation

To prepare 10,000 capsules each containing 20 mg AH 9932, for use in an insufflator for inhalation into the lung Micronise the AH 9932V to give a powder in which nearly all particles are smaller than 5 μm diameter. Blend 220 g of micronised drug with 200 g of lactose B.P., previously sieved through 200 mesh and over 300 mesh sieves. Fill the powder blend into No. 3 hard gelatin capsules on a suitable machine, so that each capsule contains 42 mg of powder.

The active materials AH 9932 and AH 9932V may be replaced by another compound according to the invention if desired.

We claim:

1. A compound of the formula

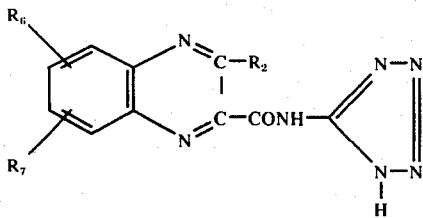

or a pharmaceutically acceptable salt thereof in which: $R_2$ represents a hydrogen atom, a halogen atom, an alkyl group or the group $OR_3$, where $R_3$ is a hydrogen atom, an alkyl group or an alkyl group substituted by at least one alkoxy or hydroxy group; and $R_6$ and $R_7$ which may be the same or different each has the same meaning as $R_2$.

2. A compound as claimed in claim 1 in which $R_2$ represents a hydrogen atom.

3. A compound as claimed in claim 1 in which $R_6$ and $R_7$ each represent hydrogen, halogen, alkyl or alkoxy.

4. An alkali metal salt of a compound as claimed in claim 1.

5. An organic amine salt of a compound as claimed in claim 1.

6. A compound as claimed in claim 1 which is N(1H-tetrazol-5-yl)-2-quinoxalinecarboxamide.

7. A compound as claimed in claim 1 which is N(1H-tetrazol-5-yl)-2-quinoxalinecarboxamide, sodium salt, monohydrate.

8. A compound as claimed in claim 1 which is 3-chloro-N(1H-tetrazol-5-yl)-2-quinoxalinecarboxamide.

9. A compound as claimed in claim 1 which is 3(2-hydroxyethoxy)-N(1H-tetrazol-5-yl)-2-quinoxalinecarboxamide.

10. A compound as claimed in claim 1 which is 3-(2-methoxyethoxy)-N(1H-tetrazol-5-yl)-2-quinoxalinecarboxamide.

11. A compound as claimed in claim 1 which is 3-methoxy-N(1H-tetrazol-5-yl)-2-quinoxalinecarboxamide.

12. A compound as claimed in claim 1 which is 3,6-dimethoxy-N(1H-tetrazol-5-yl)-2-quinoxalinecarboxamide.

13. A compound as claimed in claim 1 which is 6,7-dimethoxy-N(1H-tetrazol-5-yl)-2-quinoxalinecarboxamide.

14. A compound as claimed in claim 1 which is 6-chloro-3-methoxy-N(1H-tetrazol-5-yl)-2-quinoxalinecarboxamide.

15. A compound as claimed in claim 1 which is 3,6,7-trimethoxy-N(1H-tetrazol-5-yl)-2-quinoxalinecarboxamide.

16. A compound as claimed in claim 1 which is 3-chloro-6,7-dimethyl-N(1H-tetrazol-5-yl)-2-quinoxalinecarboxamide.

17. A compound as claimed in claim 1 which is 6,7-dimethyl-N(1H-tetrazol-5-yl)-2-quinoxalinecarboxamide.

* * * * *